US00PP11460P

United States Patent [19]

van Rijn

[11] Patent Number: Plant 11,460

[45] Date of Patent: Jul. 25, 2000

[54] ANTHURIUM PLANT NAMED 'ESTHER'

[75] Inventor: Leonardus van Rijn, Schipluiden, Netherlands

[73] Assignee: Rijnplant B.V., Schipluiden, Netherlands

[21] Appl. No.: 09/177,292

[22] Filed: Oct. 22, 1998

[51] Int. Cl.[7] ..... A01H 5/00

[52] U.S. Cl. ..... Plt./365

[58] Field of Search ..... Plt./365, 367, 368

*Primary Examiner*—Howard J. Locker
*Assistant Examiner*—Kent L. Bell
*Attorney, Agent, or Firm*—C. A. Whealy

[57] ABSTRACT

A distinct cultivar of Anthurium plant named 'Esther', characterized by its upright, outwardly arching and very freely clumping growth habit; rapid growth rate and vigorous; strong rooting system; durable dark green leaves that are ovate in shape; numerous inflorescences that are positioned just above the foliage on strong and erect scapes; durable pink spathes; year-round continuous flowering; and good post-production longevity.

2 Drawing Sheets

BACKGROUND OF THE INVENTION

The present invention relates to a new and distinct cultivar or Anthurium plant, botanically known as *Anthurium andreanum*, and hereinafter referred to by the cultivar name 'Esther'.

The new Anthurium is a product of a planned breeding program conducted by the Inventor in Schipluiden, The Netherlands. The objective of the program is to create new Anthurium cultivars that have a freely clumping growth habit, strong plant and root growth, attractive spathe color, numerous inflorescences and leaves, and good post-production longevity.

The new Anthurium originated from a cross by the Inventor on Aug. 10, 1993 of the Inventor's proprietary *Anthurium andreanum* selection code number 93-9 as the female, or seed, parent with the Inventor's proprietary *Anthurium andreanum* selection code number 92-2 as the male, or pollen, parent. The cultivar Esther was discovered and selected by the Inventor as a plant within the progeny of the stated cross in a controlled environment in Schipluiden, The Netherlands in Aug., 1995.

Asexual propagation of the new cultivar by tissue culture in a laboratory in Belgium has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar 'Esther'. These characteristics in combination distinguish 'Esther' as a new and distinct cultivar:

1. Upright, outwardly arching and very freely clumping growth habit.
2. Rapid growth rate and vigorous.
3. Strong rooting system.
4. Durable dark green leaves that are ovate in shape.
5. Numerous inflorescences that are positioned just above the foliage on strong and erect scapes.
6. Durable pink spathes.

7. Year-round continuous flowering.
8. Good post-production longevity.

The new Anthurium can be compared to the female parent, the Inventor's proprietary selection code number 93-9. In side-by-side comparisons conducted by the Inventor in Schipluiden. The Netherlands, plants of the new Anthurium differ from plants of selection code number 93-9 in the following characteristics:

1. Plants of the new Anthurium have pink-colored spathes whereas plants of the selection code number 93-9 have red-colored spathes.
2. Plants of the new Anthurium have a more rapid growth rate than plants of the selection code noumber 93-9.
3. Plants of the new Anthurium have more durable, glossier and rougher leaves than plants of the selection code number 93-9.

The new Anthurium can be compared to the male parent, the Inventor's proprietary selection code number 92-2. In side-by-side comparisons conducted by the Inventor in Schipluiden, The Netherlands, plants of the new Anthurium differ from plants of selection code number 92-2 in the following characteristics:

1. Plants of the new Anthurium have darker pink-colored spathes than plants of the selection code number 92-2.
2. Plants of the new Anthurium have rougher leaves than plants of the selection code number 92-2.

Plants of the new Anthurium have smaller spathes than plants of the selection code 92-2.

3. Plants of the new Anthurium have smaller spathes than plants of the selection code number 92-2.

The new Anthurium can be compared to the Anthurium cultivar 'Elisabeth' disclosed in U.S. Plant Pat. No. 9,704. In side-by-side comparisons conducted by the Inventor in Schipluiden, The Netherlands, plants of the new Anthurium differ from plants of the cultivar 'Elisabeth' in the following characteristics:

1. Plants of the new Anthurium have flatter, more durable, more rounds, and rougher leaves than plants of the cultivar 'Elisabeth'.
2. Plants of the new Anthurium have smaller spathes that plants of the cultivar 'Elisabeth'.

BRIEF DESCRIPTION OF THE PHOTOGRAPHS

The acompanying colored photographs illustrate the overall appearance of the new Anthurium, showing the colors as true as it is reasonably possible to obtain in colored reproductions of this type. The photograph on the first sheet comprises a top perspective view of a typical potted plant of the cultivar 'Esther'. The photograph on the second sheet comprises a close-up view of a typical spathe and spadix of the cultivar 'Esther'. Leaf, spathe and spadix colors in the photogrpahs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe seven-month old plants grown in Schipluiden, The Netherlands, in a glass greenhouse with an average day temperation of 25° C. and an average night temperature of 19° C.

Botanical classification: *Anthurium andreanum* cultivar 'Esther'.

Parentage:

*Female parent.*—Inventor's proprietary *Anthurium andreanum* selection code number 93-9.

*Male parent.*—Inventor's proprietary *Anthurium andreanum selection code number* 9-2.

Propagation:

*Method.*—Typically by tissue culture.

*Time to initiate roots.*—Abouth 70 or 84 days at 24° C or 21° C, respectiely.

*Rooting habit.*—Numerous and very strong fleshy roots.

Plant description:

*Plant Shape.*—Upright, inverted triangle, symmetrical.

*Growth habit.*—Erect when young, becoming outwardly arching as leaves develop. Freely clumping, bushy and dense. Appropriate for 19 to 40-cm containers.

*Plant height.*—About 40 cm from soil level to apex of spathes.

*Plant vigor.*—High.

*Growth rate.*—Rapid.

*Crop time.*—About 9 months are usually required from planting of young plants to finished plants in 19-cm containers.

*Foliage description.*—Quantity: Usually about 23 leaves per container. Length: About 26 cm. Width: About 17.5 cm. Shape: Ovate. Apex: Apiculate to cuspidate. Base: Auriculate to cordate; lobes not overlapping. Margin: Entire, slight undulation. Texture: Smooth, glabrous, leathery. Color: Young leaves, upper surface: 144A. Young leaves. lower surface: 144C to 144A to 147C. Mature leaves, upper surface: Between 139A. and 137A. Mature leaves, lower surface: Darker than 144A. Petiole: Length: About 30 cm. Color: 144A. Geniculum length: About 2.5 cm.

Inflorescence Description:

*Inflorescence arrangement.*—Spathe with spadix held above the foliage. Flowering structures arise from leaf axils. Freely flowering; continuous flowering year-round; typically three to six inflorescences per plant. Not fragrant.

*Inflorescence longevity.*—Inflorescences last about six weeks under winter conditions and up to three months under summer conditions; persistent.

*Flowers.*—Quantity per spadix: Numerous, about 150. Shape: Rounded. Diameter: About 1 mm, maximum.

*Spathe.*—Length: About 6 cm. Width: About 8 cm. Height about foliage: About 10 cm. Shape: Deltoid. Apex: Apiculate to mucronate. Base: Auriculate to cordate; lobes not overlapping. Margin: Entire. Texture: Leathery, glabrous, some blistering, shiny. Color: When opening: 38A. Front surface: 49A to 49B. Back surface: 49B to 49C.

*Spadix.*—Length: About 5 cm. Diameter: About 8 mm. Shape: Columnar. Cross section: Rounded. Longitudinal axis: Straight, erect. Color: Base: Creamy white, 159A. Mid-section: 159A. Apex: 25C.

*Scape.*—Length: About 30 cm. Aspect; Strong and erect. Color: 144A with anthocyanin towards apex.

*Reproductive organs.*—Androecium: Pollen color: Creamy white, 159D. Gynoecium: Stigma shape: Ovoid.

Disease resistance.—Plants of the new Anthurium have not been shown to be resistant to diseases common to Anthurium.

*Seed development.*—Seed development on plants of the new Anthurium has not been observed.

It is claimed:

1. A new and distinct cultivar of Anthurium plant named 'Esther', as illustrated and described.

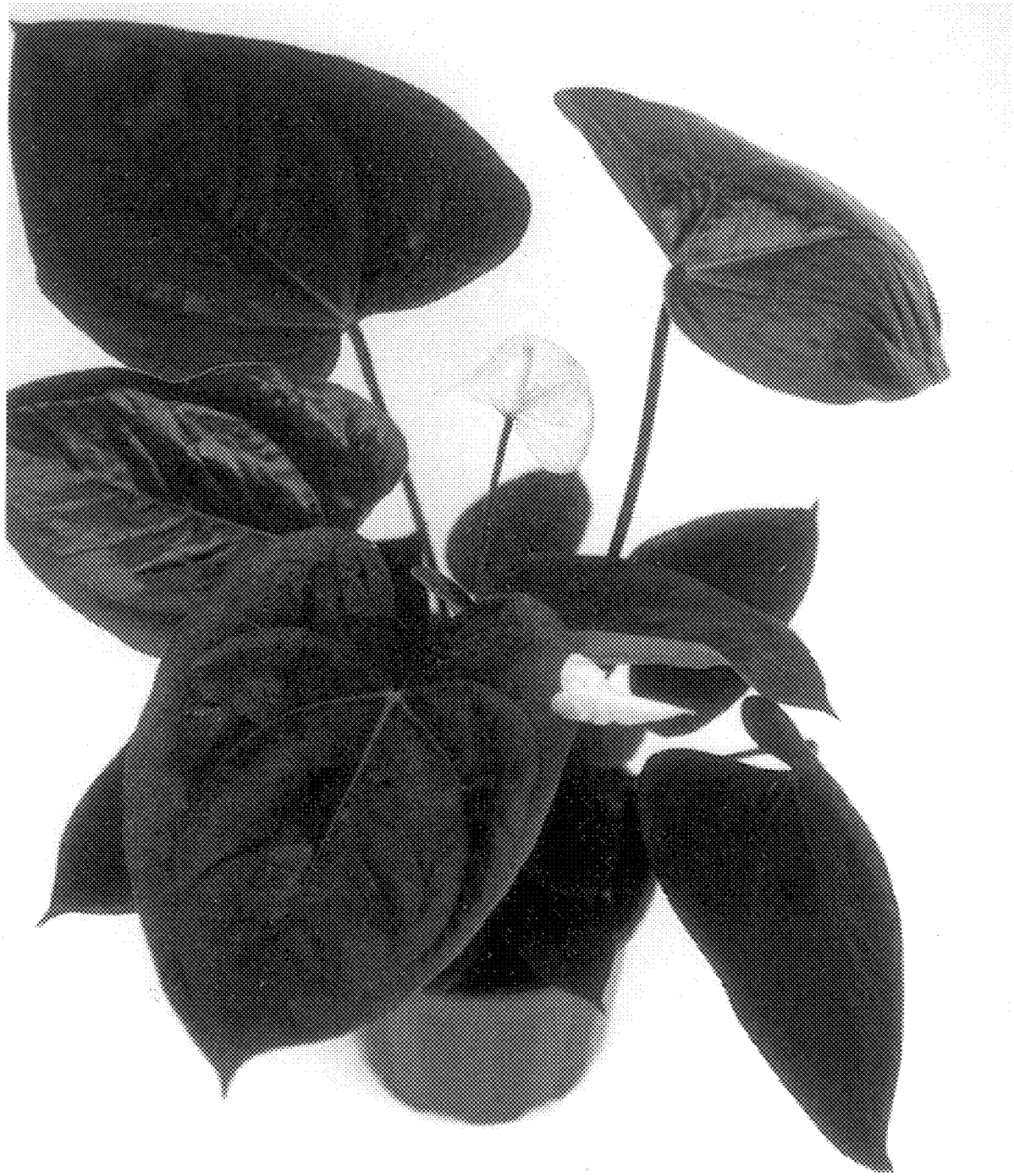

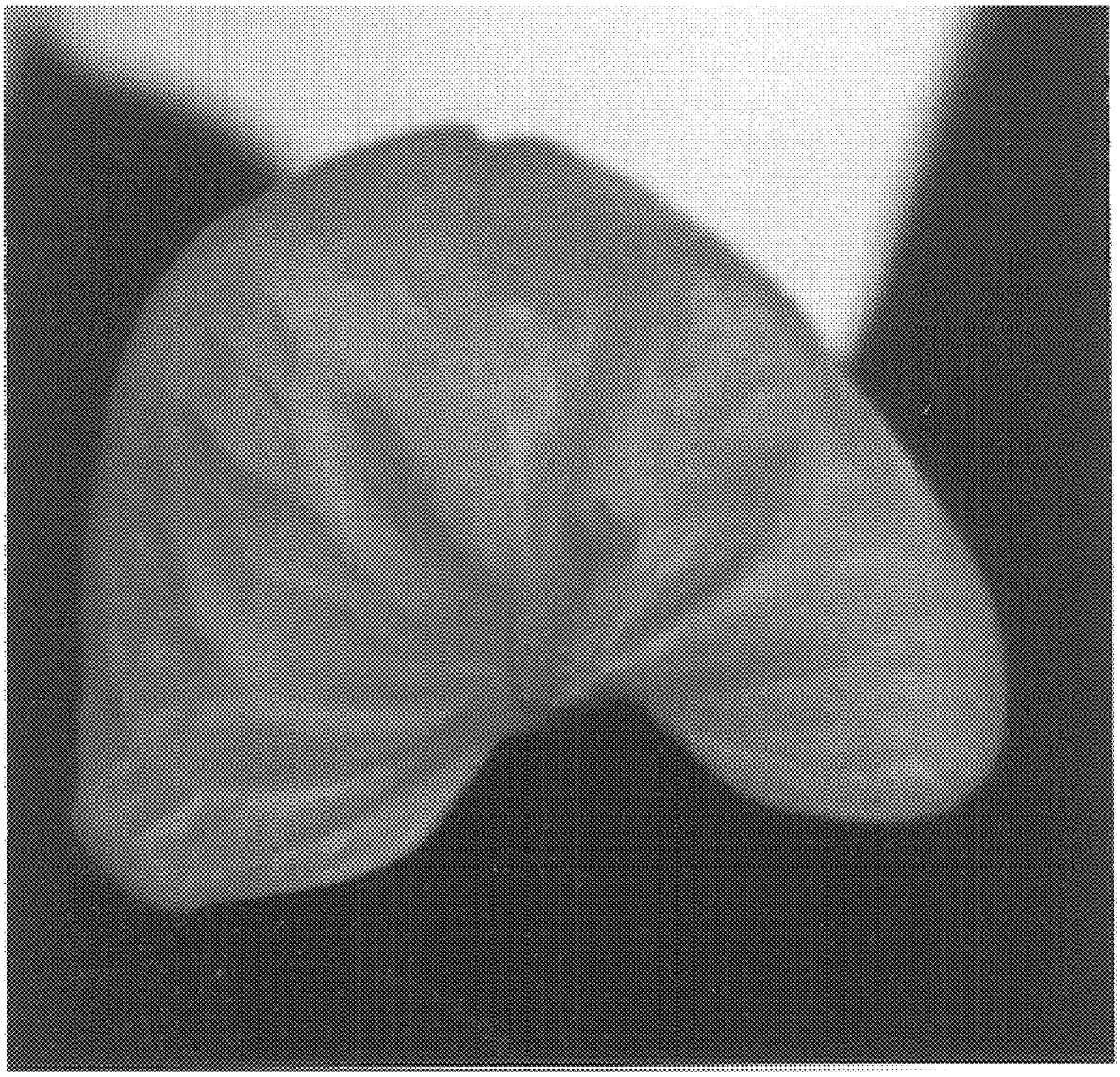

* * * * *